United States Patent [19]

Rising et al.

[11] Patent Number: 4,966,667
[45] Date of Patent: Oct. 30, 1990

[54] GEL TRANSFER PROCESS AND COMPOSITE

[75] Inventors: Donald B. Rising, Stow; Rita Zimmerman, West Roxbury, both of Mass.

[73] Assignee: Millipore Corporation, Bedford, Mass.

[21] Appl. No.: 340,107

[22] Filed: Apr. 18, 1989

[51] Int. Cl.⁵ .................. G01N 27/26; B01D 57/02
[52] U.S. Cl. .................. 204/182.1; 204/299 R; 204/182.8
[58] Field of Search ............ 204/182.1, 182.8, 290 R, 204/180.1, 182.9

[56] References Cited

U.S. PATENT DOCUMENTS 4,305,799  12/1981  Schwarz et al. .............. 204/182.1
4,874,490  10/1989  Hochstrasser ................ 204/182.1

FOREIGN PATENT DOCUMENTS 58-193446  11/1983  Japan ...................... 204/180.1
60-169597   9/1985  Japan ...................... 204/180.1
62-075248   4/1987  Japan ...................... 204/299 R

*Primary Examiner*—John F. Niebling
*Assistant Examiner*—John S. Starsiak, Jr.
*Attorney, Agent, or Firm*—Andrew T. Karnakis; Paul J. Cook

[57] ABSTRACT

An apparatus and process are provided for transferring a gel shaped as a cylinder containing a treated sample from a first step to a second electrophoresis step without distorting the position of the treated sample within the shaped gel. A shaped gel useful in electrophoresis is formed in a tube with a multifilament thread extending the entire length of and within the central portion of the shaped gel. The shaped gel then is employed in a first treatment step to form a treated sample that may be a separated sample. After extrusion of the gel from the tube, the portion of the thread extending from each end of the shaped gel is grasped and the shaped gel containing the treated sample is transferred to contact a slab gel along the entire length of the shaped gel to effect an electrophoresis step in the second treatment step.

9 Claims, 1 Drawing Sheet

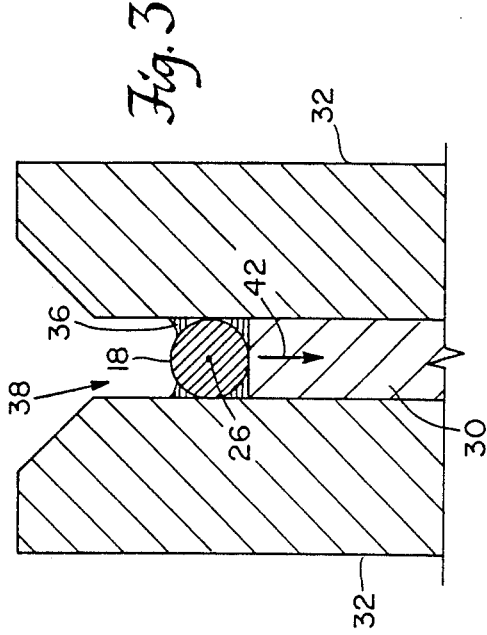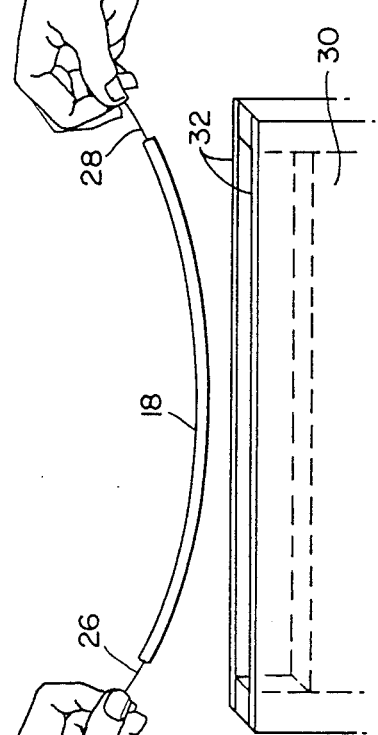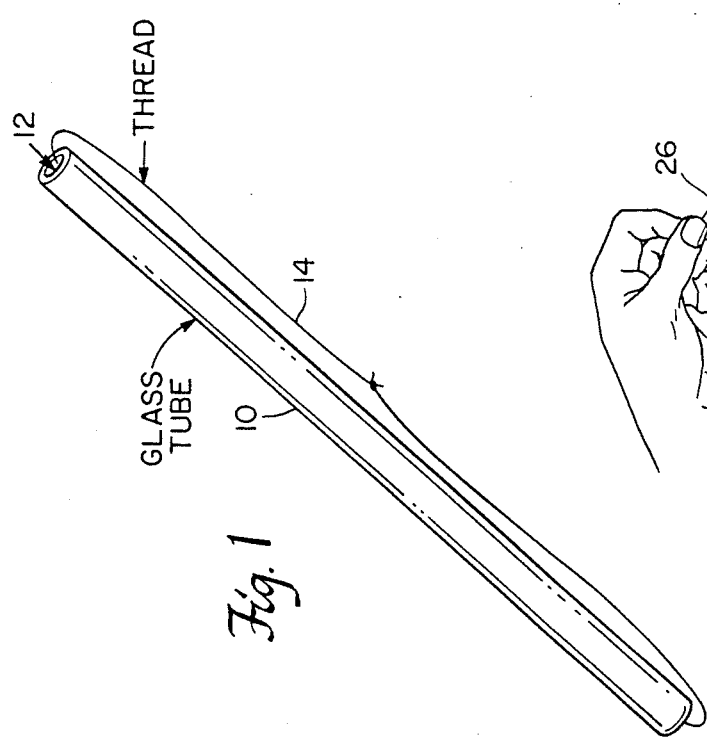

GEL TRANSFER PROCESS AND COMPOSITE

BACKGROUND OF THE INVENTION

This invention relates to a process for conducting a two-step sample treatment process in a gel which involves a step of transferring a shaped gel cylinder containing samples from a first step of treatment to a second sample separation step.

Electrophoresis is the resolution of a complex mixture of macromolecules on the basis of charge and/or size under the influence of an electric field and is a primary tool in analytic chemistry, used to separate complex mixtures of molecules such as proteins into their individual components. Electrophoretic analysis is based upon the fact that each molecule is characterized by a particular electrophoretic mobility under a given set of conditions. Macromolecules will migrate within a voltage gradient according to their net charge and will reach equilibriun at their isoelectric point at which their net mobility will be zero. For example, many proteins exhibit a net negative charge which is affected by the surrounding pH. When a mixture of proteins is placed in a support medium, such as a buffered gel, which is subjected to a voltage gradient, each component is caused to migrate through the support medium at its characteristic rate for that set of conditions. Electrophoretic mobility is a function of net charge, molecular weight, shape and a number of other factors which are controlled by experimental conditions.

Two dimensional gel electrophoresis permits resolution of complex proteins on the basis of charge in one step and on the basis of molecular size in a second step. Either size separation of charge separation can be conducted in the first step. As part of the first step, the sample is added to a shaped gel cylinder which has been cast in a narrow tube, e.g, 3 mm or less diameter or maximum cross sectional dimension, which gel is characterized by a pH gradient. Generally, the top of the gel cylinder has a basic pH of about 10-13 and the bottom of the gel cylinder has an acidic pH of about 2-5 or other pH ranges could be used. A pH gradient is established over the length of the gel. The sample is placed on the gel which then is subjected to a voltage gradient which, in turn, causes the constituents of the sample to migrate through the gel to the point at which the constituent is electrically neutral, i.e., the isoelectric point.

After making the isoelectric focussing separation, the gel is carefully extruded from the tube into an equilibration or storage buffer, and then transferred onto the edge of a second separation medium such as a membrane or a gel slab for the second dimension separation. In the second dimension separation, the sample constituents are separated on the basis of molecular size, charge etc. Numerous methods have been employed to effect this transfer, but it is an extremely difficult laboratory procedure. This is in large part due to the extraordinary fragility of the first dimension gel which cannot support its own weight in air and must be handled under a liquid or on a solid surface to maintain integrity. Typically the gel is pressure extruded from the tube as a glass tube into a buffer solution, care being taken to keep the end of the tube entirely submerged in the buffer during extrusion. The top of the second separation medium to which the shaped gel is to be applied is submerged under an electrophoresis buffer, and the transferred gel cylinder is manipulated commonly under liquid onto the edge of the second gel by careful manipulation with probes and forceps.

Even when handled under liquid, the gel can be readily stretched if insufficient care is not taken thus causing distortion of the resultant final electrophoretic pattern, or even broken while attempting to maneuver the cylinder onto the slab gel. Furthermore, the first dimension gel will tenaciously adhere to a dry surface, if inadvertently contacted during a transfer operation. Therefore, these cylindrical gels often are transferred from their original tube to the slab gel entirely under liquid. This poses an additional problem. The gel is completely transparent and has almost the same refractive index as the buffer solutions used. As a consequence it is extremely difficult to even see the gel during transfer operations, in addition to the mechanical handling problems.

Accordingly, it would be highly desirable to provide a means that allows easy mechanical transfer without distortion and breakage of the gel cylinder. Furthermore, such means should reduce the extraordinary dexterity skills presently required to effect transfer of the gel cylinder.

SUMMARY OF THE INVENTION

This invention is based on the discovery that a multifilament thread molded within a cylindrical gel which is to be used subsequently in electrophoresis can support the cylindrical gel without distorting it and without cutting through the gel under the burden of its own weight. The gel composition having a multifilament thread extending through its length is molded within a cylindrical tube having an inner diameter or largest cross sectional dimension between about 1 and about 3 mm. The cylindrical gel after being used to process a sample under a voltage gradient within the cylindrical tube is first extruded from the tube into the equilibration or storage buffer. When it is desired to transfer the cylindrical gel to the next electrophoresis step, a portion of the thread extending from one or both ends of the cylindrical gel is grasped. The cylindrical gel then is lifted by the thread and transferred to contact a a gel matrix in order to effect a second electrophoresis step wherein the molecules separated within the cylindrical gel are subjected to a second voltage gradient to effect migration of the molecules through the gel matrix. The transfer step of this invention is far simpler and far more reliable than the transfer techniques of the prior art. As the cylindrical gel is not distorted by use of this invention, the resulting electrophoretic patterns are more reproducible. As used herein the term "cylinder" or "cylindrical" means an elongated solid having a major axis and a cross sectional plane perpendicular to the major axis which can have any shape such as circular, elliptical, square, rectangle, trapezoid, triangular, parallelogram, etc.

BRIEF DESCRIPTION OF THE DRAWINGS

FIG. 1 is a side view of the mold useful for forming the cylindrical gel structure of this invention.

FIG. 2 illustrates the method of placing the cylindrical gel on a slab gel matrix.

FIG. 3 is a cross-sectional view of the gel cylinder positioned on a slab shaped gel matrix.

DESCRIPTION OF SPECIFIC EMBODIMENTS

This invention provides a method and composite product for transferring a fragile cylindrical gel which can contain a separated molecular sample from one sample processing step to a second sample processing step. The cylindrical gel generally has a diameter or largest cross sectional dimension of between about 1 and 3 mm and has a multifilament thread extending the length of the cylindrical gel and protruding from each end thereof. The cylinder is foremed of a gel composition normally employed in electrophoresis such as agar gel, agarose gel or polyacrylamide gel which includes an appropriate buffer as is well known in the art and which is molded about the multifilament thread which is preferably under slight tension. The two step electrophoresis process is referred to as two-dimensional electrophoresis. In the first step, the gel is formed with the thread within a cylindrical mold, a sample is placed on one end surface of the gel and the gel is subjected to a voltage gradient to effect isoelectric focusing of the sample.

The gel and thread containing the separated sample then is extruded from the cylindrical tube with a water buffer into an equilibration or storage buffer. Thereafter the protruding thread end or ends are grasped and the cylindrical gel is transferred to a second electrophoresis step where the cylindrical gel is contacted with a second gel along its length and the second gel is subjected to a voltage gradient in the presence of a suitable buffer. Surprisingly, it has been found that a monofilament thread is not useful in the present invention since it will cut through the cylindrical gel when it is used to lift the cylindrical gel. The multifilament thread can be twisted, braided, etc. and formed from either synthetic fibers such as polyester, polyamide or the like or natural fiber such as cotton. The molecules previously separated along the length of the cylindrical gel then migrate into the second gel without interference by the thread and are separated further within the second gel. In this manner, the sample is separated on the basis of two physical characteristics of the molecules in the sample, first in the cylindrical gel and then in the second gel.

Referring to FIG. 1, a hollow cylinder 10 is shown having a bore 12 that extends the length of the cylinder 10. An electrophoresis gel composition is injected into bore 12 to produce a gel within bore 12 and surrounding thread 14. After the gel is formed within cylinder 10, the first electrophoresis step is conducted within cylinder 10 in the manner set forth above. The cylindrical gel and thread then are extruded from cylinder 10.

The cylindrical gel and thread then are transported to contact a slab as shown in FIGS. 2 and 3. As shown in FIG. 2, the protruding ends 26 and 28 of thread 14 are grasped and the cylindrical gel is lifted to contact slab 30 positioned within plates 32. The cylindrical gel 18 is positioned on slab gel 30. Liquid buffer 36 is added to the slot 38 to facilitate the second electrophoresis step. In the second electrophoresis step, the molecules within cylindrical gel 18 migrate into slab gel 30 in the direction shown by arrow 42. The cylindrical gel can be formed with only one end of the thread protruding from the gel if desired.

The following example illustrates the present invention and is not intended to limit the same.

EXAMPLE I

A gel composition comprising a 2.7% polyacrylamide in 9.5M urea solution was injected into a glass tube having an inner diameter of 1 mm and allowed to gel for 1 hour. The gel was formed about a two-strand multifilament polyester thread which was under slight tension and which extended through the tube its length. Electrophoresis was conducted by injecting overlay buffer of dilute urea/beta mercaptoethanol solution into the basic end of the tube and prefocused, followed by injection of a sample of protein. Electrophoresis was conducted at a voltage of 1000 V over a period of 18 hours. The resultant cylindrical gel and sample separated therein was extruded from the tube with water into an equilibration buffer of TRis/SDS. The cylindrical gel was transferred by grasping thread ends 26 and 28 and lifting cylindrical gel 18 to the top edge of slab gel 30 formed of 10% polyacrylamide in water. An aqueous buffer solution of Tris base was injected onto the top of slab gel 30 and the slab gel was subjected to constant power of 6.5 watts/cm$^2$ for about 4½ hours to effect sample separation within slab gel 30.

What is claimed is:

1. In a process for conducting gel electrophoresis analysis of molecule mixtures which includes a first step of separating molecules utilizing a voltage gradient within a shaped gel enclosed within a container and a second step of separating molecules within said shaped gel to a gel matrix in contact with said shaped gel utilizing a voltage gradient the improvement which comprises:

forming said shaped gel with a multifilament thread extending through the length of said shaped gel in a container such that ends of said thread extend from said shaped gel, extruding said shaped gel and thread from said container, and transporting said shaped gel and thread to contact with said gel matrix by securing said free ends of thread.

2. The process of claim 1 wherein said forming step is conducted while said thread is under tension.

3. A gel composite useful in electrophoresis which comprises a cylindrically shaped gel and a multifilament thread extending through the length of said gel to provide projecting ends of said thread extending from opposite ends of said cylinder.

4. A gel composite useful in electrophoresis which comprises a cylindrically shaped gel and a multifilament thread extending through the length of said gel to provide a projecting end of said thread extending from one end of said cylinder.

5. The composite of any one of claims 3 or 4 wherein said gel is agarose gel.

6. The composite of any one of claims 3 or 4 wherein said gel is agar gel.

7. The composite of any one of claims 3 or 4 wherein said gel is polyacrylamide gel.

8. The composite of any one of claims 3 or 4 wherein said thread is formed of synthetic fibers.

9. The composite of any one of claims 3 or 4 wherein said thread is formed of natural fibers.

* * * * *